United States Patent [19]

Wickramasinghe et al.

[11] Patent Number: 4,747,698
[45] Date of Patent: May 31, 1988

[54] SCANNING THERMAL PROFILER

[75] Inventors: Hermantha K. Wickramasinghe, Chappaqua; Clayton C. Williams, Peekskill, both of N.Y.

[73] Assignee: International Business Machines Corp., Armonk, N.Y.

[21] Appl. No.: 858,320

[22] Filed: Apr. 30, 1986

[51] Int. Cl.⁴ ............................................. G01N 25/00
[52] U.S. Cl. ........................................ 374/6; 374/124; 374/164; 136/228
[58] Field of Search ................. 374/6, 7, 45, 120, 124, 374/137, 164, 179; 136/228

[56] References Cited

U.S. PATENT DOCUMENTS

| | | | |
|---|---|---|---|
| 2,644,851 | 7/1953 | Tapke | 136/228 |
| 2,952,725 | 9/1960 | Evans et al. | 136/228 |
| 3,154,060 | 10/1964 | Hundere | 136/228 |
| 3,343,589 | 9/1967 | Holzl | 136/228 |
| 3,400,266 | 9/1968 | Yoder et al. | |
| 3,416,373 | 12/1968 | Havens | 374/6 |
| 3,430,045 | 2/1969 | Bjork et al. | 374/124 |
| 3,433,052 | 3/1969 | Maley | |
| 3,435,212 | 3/1969 | Yoder et al. | |
| 3,619,299 | 11/1971 | Weinmann | 136/228 |
| 3,810,009 | 5/1974 | Hausler et al. | 374/7 |
| 3,913,378 | 10/1975 | Hausler | 347/7 |
| 3,973,122 | 8/1976 | Goldberg | |
| 4,343,993 | 8/1976 | Binnig et al. | |
| 4,510,390 | 4/1985 | Rajchman | 374/6 |
| 4,522,510 | 6/1985 | Rosenwaig et al. | 374/7 |

OTHER PUBLICATIONS

"Tiniest Tools Probe a Cell's Molecules," *Science News*, vol. 128, Sept. 14, 1985, p. 167.

*Primary Examiner*—William A. Guchlinski, Jr.
*Assistant Examiner*—Thomas B. Will
*Attorney, Agent, or Firm*—Perman & Green

[57] ABSTRACT

Apparatus is provided for investigating surface structures irrespective of the materials involved. A fine scanning tip is heated to a steady state temperature at a location remote from the structure to be investigated. Thereupon, the scanning tip is moved to a position proximate to, but spaced from the structure. At the proximate position, the temperature variation from the steady state temperature is detected. The scanning tip is scanned across the surface sturcture with the aforesaid temperature variation maintained constant. Piezo electric drivers move the scanning tip both transversely of, and parallel to, the surface structure. Feedback control assures the proper transverse positioning of the scanning tip and voltages thereby generated replicate the surface structure to be investigated.

21 Claims, 6 Drawing Sheets

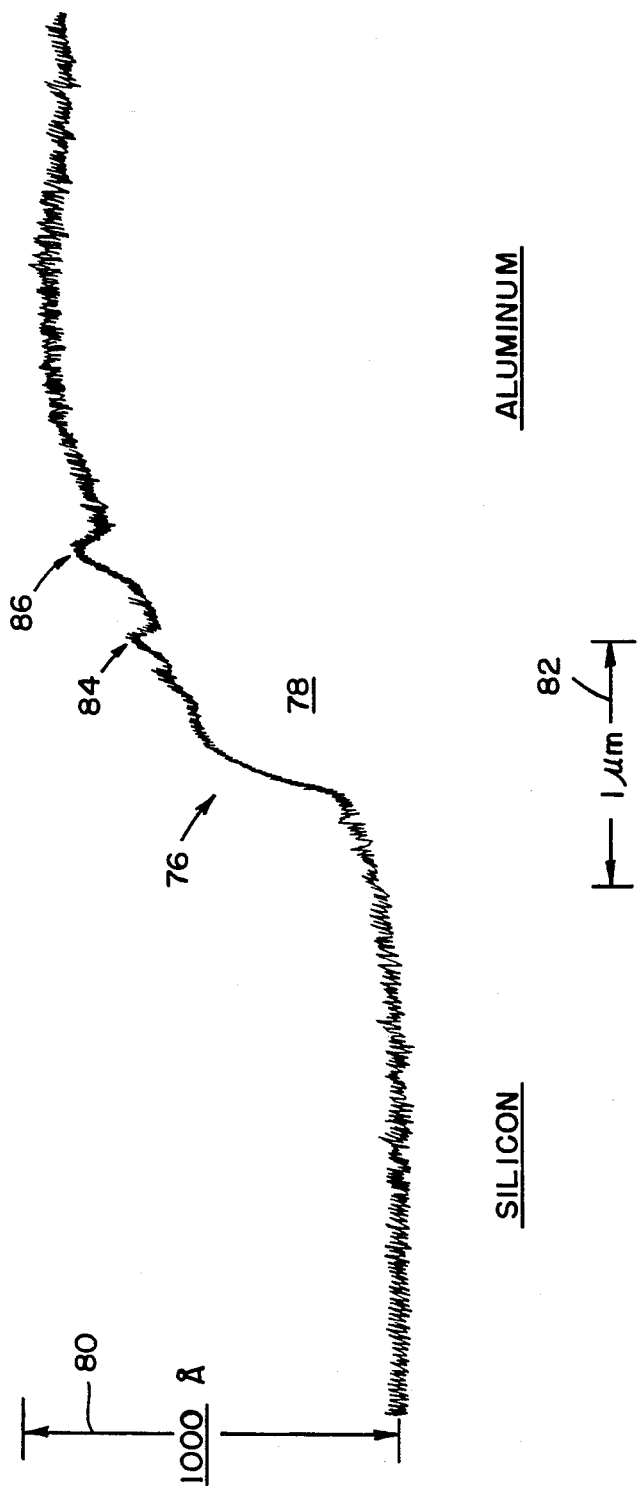

SCANNING THERMAL PROFILER

FIELD OF THE INVENTION

The present invention relates to an improved method and apparatus for the investigation and topographical measurement of miniature surface structures with ultra-high resolution and without concern for the type of material being investigated.

There is a substantial interest in the area of manufacturing for a high resolution, non-contact profiler with the capability to obtain a three-dimensional map of an arbitrary surface topography with sub-micron resolution. The examples of uses to which such a tool would be put are numerous, and include verification of profile of etched lines and vias in semiconductors, conductors and insulators, measurement of film thickness, surface roughness, biological investigations, and the like. As the dimensions of devices on VLSI wafers are further reduced, the ability to monitor and measure the geometric parameters becomes increasingly important. The ability to measure these structures in a non-contact, non-material dependent fashion is an important measurement need both for development and manufacturing purposes.

DESCRIPTION OF THE PRIOR ART

A well known method for investigation of surface structures is by visual inspection with the human eye. However, there are natural boundaries for optical resolution with the naked eye. Optical instruments can be used to further improve optical resolution. However, even with the best optical instruments, limits are reached which are imposed by the nature of light.

Resolution can be further improved using apparatus operating with radiation of effective wave-length which is shorter than visible light, such as performed by the electron microscope. However, there are a number of recognized difficulties with the electron microscope. In the first instance, the electron microscope operates in a vacuum. Another drawback resides in its inability to obtain geometric profiles of large steps. Accurate results are also difficult to obtain when an electron microscope is used to investigate structures on insulator materials because of electron charging of the insulation surfaces. In comparison with optical microscopes, lateral resolution is improved remarkably. However, vertical resolution is greatly limited by reason of its inherently large depth of field.

Apparatus for investigation of surface structures operates either with electromagnetic radiation or with a corpuscular radiation interacting with the surface of the sample. Strictly speaking, instruments capable of resolving structures in the atomic or molecular range do not image a surface in the sense of producing an image for visual inspection. However, such instruments do provide information sufficient to allow conclusions to be made about the structure and composition of the surface of the sample. For example apparatus exists for observation of selective diffraction of low energy electrons at a surface (LEED). Another apparatus uses secondary ion mass spectroscopy (SIMS).

The term microscopy is used where a surface is imaged with radiation of the same energy. Where radiation of different voltages or frequencies is used, i.e., with varying energy, the term spectroscopy is generally used. Dual purpose instruments are usually called microscopes even if they allow spectroscopic investigations as well.

All these known instruments require that the surface investigations be made in a good vacuum. Temperatures should be as low as possible in the cryogenic range. The particles used are free particles moving in a high vacuum under the influence of applied fields. These particles need to be freed previously, of course, by some cathode or ion source.

A major recent advance in the investigation of surface structures has been disclosed in commonly assigned U.S. Pat. No. 4,343,993 issued Aug. 10, 1982 to Binnig et al. That invention relates to apparatus utilizing the vacuum tunnel effect. To that end, an ultra-high vacuum chamber is cooled down to a cryogenic temperature in the vicinity of absolute zero. A conductive sample is placed in this UHV chamber and serves as a base electrode with respect to a fine conductive tip that serves as a scanning electrode. The scanning electrode is poised above the base electrode at a distance of only a few Angstroms.

In an atomic system or in a solid body, if charged particles are subjected to an interaction composed of a long range repelling component and a short range attractive component, then the resulting force builds a potential wall or a barrier. According to classical conceptions, such a barrier can be crossed only by particles having energy greater than the barrier. There are nevertheless always a finite number of particles by a potential barrier which are capable of crossing the potential barrier even though they do not have sufficient energy. In a sense, they undercross the potential barrier via a tunnel. This so-called tunnel effect can be explained only by wave mechanics. Atomic particles have a two-fold nature in that only part of their properties can be explained by particle mechanics, another part of their properties being interpreted only by the wave concept. The tunnel effect is a wave property comparable in a sense with the wave matching phenomenon at an interface between different media.

According to the tunnel effect, there exists a calculable probability that a finite number of electrons bound by a potential can cross the tunnel barrier even at low voltage differences. A tunner barrier may be provided by a thin layer in a solid body. A high vacuum may also represent a tunnel barrier when the high vacuum distance to be crossed is between a few and several hundred Angstroms. Some bound electrons are capable of tunneling through such distances. In earlier experiments with vacuum tunnel barriers, a very weak tunneling current flowed from a fine conductive tip to a flat counter electrode when the tip was poised above the counter electrode within a small distance. However, prior to the Binnig et al development, experiments required expensive apparatus and were time-consuming due to considerable technical difficulties. Many hours were often needed to obtain a single measuring point. A series of measurements required several days.

Prior to the Binnig et al invention, experiments with field electron emission had also been carried out wherein a fine tip served as an electron source or as a so-called cold cathode. Under the influence of a strong electrical field, electrons are freed from the emitting tip and are accelerated towards, and kind of imaged upon, a screen or photosensitive layer. The distances traveled in the vacuum by the electrons are considerably longer than the required short distance within which the vacuum tunnel effect is possible with bound electrons. In Binnig et al, however, the tunnel effect is utilized only to free electrons from the metal of the tip through the vacuum to the surface being investigated, or vice versa.

Although the scanning tunneling microscope represented a significant improvement when it was devised, nonetheless, in order to implement such an instrument, considerable technical difficulties had to be overcome. The apparatus must generally operate in an ultra-high vacuum of better than $10^{-10}$ Torr. Furthermore, the temperature should be as close to absolute zero as possible. This means cryogenic temperature lower than liquid helium temperature of 4.2° K. The operating temperature should be lower than 1° K. and preferably lower than 0.3° K. Under these extreme conditions, position adjusting drives should still operate and have sensitivity on the order of Angstroms. The drives should also be capable of being positioned accurately and reproducibly. A vertical drive is especially difficult to implement. On the one hand it must move in a relatively coarse fashion over a distance in the range of millimeters at the beginning of an investigation, when the apparatus is loaded with a sample to be investigated. But during the actual investigation, it must be capable of operating very finely with an accuracy on the order of fractions of an Angstrom. Special attention should be directed towards obtaining absolute freedom from vibrations. Thermal fluctuations, which normally produce variations on the order of magnitude of Angstroms, and hence in the order of magnitude of the operating range of the instrument, have already been substantially removed by the extreme cooling down. However, every sound pulse, no matter how small, will generate a disturbing elastic wave within the material. Therefore, an optimal suspension or support of the essential parts of the instrument is also very important.

SUMMARY OF THE INVENTION

It was with knowledge of the prior art and the problems existing which gave rise to the present invention. For example it was sought to obtain the benefits achieved by the scanning tunneling microscope, especially its ability to obtain high resolution, high speed, non-destructive graphic displays of miniature surface structures, but without its drawbacks. For example the scanning tunneling microscope is limited to measuring conductive and semi-conductive surfaces whereas the present invention is material independent. Also, the scanning tunneling microscope can accurately measure only relatively small rates of change of topography (up to approximately a 20 Angstrom change in the vertical dimension for every 100 Angstrom change in the horizontal dimension) whereas the present invention can accommodate topography exhibiting much larger magnitudes and rates of change of topography. Another significant benefit of the present invention resides in the fact that it does not require super cooling or a vacuum as does the scanning tunneling microscope, but the technique can be performed in a broad range of atmospheres and temperatures.

The present invention, then, is a high resolution noncontact profilometer which has the potential to measure the topographical features of an arbitrary surface with lateral resolution below 300 Angstroms and depth resolution below one Angstrom. It is based upon a principle which is similar in concept to that of a scanning tunneling microscope. However, the coupling between a very small tip and the surface (solid or liquid) to be investigated is a thermal interaction rather than one based on an electron tunneling current.

The basic element of the profilometer is a temperature sensor such as a thermocouple which can be made with very small dimensions. As early as 1972, tungsten tips with tip diameters of approximately 100 Angstroms were controllably produced using electropolishing techniques. To create a very small thermocouple, such a tip can be electrically insulated with a thin insulator or dielectric material over all regions of the tungsten material except for a small region near the tip. If the tungsten and insulator is then coated with a thin layer of a conducting or semi-conducting material other than tungsten, a thermocouple junction results at the tip. The thermoelectric voltage generated at the tip can be sensed at the far end of the tungsten probe by measuring the voltage differential between the inner and outer conductors. This provides a means for measuring the local temperature over a volume which can be as small as $10^{-24}$ cubic meters.

If current is driven through the junction at a frequency $f_1$, after a short initial time, the tip arrives at some steady state temperature at twice the frequency of the drive current $2f_1$. The magnitude of this sinusoidal, or even dc temperature, depends upon the extent of the heat transfer between the tip and the surrounding environment, i.e. the "thermal loading" on the tip. When the tip is then brought close to the solid surface, the tip becomes thermally loaded and its temperature is thereby affected by the presence of the solid surface due to theat being drawn away from the tip through the surrounding medium, then into the material of the solid surface. A vertical vibration of the tip at frequency $f_2$ modulates the distance between tip and sample, and correspondingly modulates the temperature loading caused by the solid surface. This generates a temperature variation in the thermocouple tip at the difference frequency $(2f_1 - f_2)$. The magnitude of the signal at the difference frequency depends upon the average position of the probe relative to the surface. When the tip is then scanned laterally across the surface, the size of the signal at the difference frequency is modulated by any surface topography. However, rather than extract the topographical information this way, a servo loop is used to adjust the average position of the tip relative to the surface such as to maintain the signal at the difference frequency constant while scanning laterally over the surface. The error (or feedback) signal necessary to maintain the magnitude of the difference frequency signal constant is then a replica of the topography of the solid. In this way, one maintains a constant signal/noise ratio across the entire scan area.

Since the probe tip is both the source and the detector of the thermal distribution, the profile can be obtained without contacting the surface being investigated. Another attractive feature of such an approach is that the thermal impedance of air, through which the heat will likely pass from the tip to the surface being investigated, is very large compared to any solid or liquid, including insulators, semiconductors, and metals. This mismatch makes possible material independent profiling. This means that a profile can be obtained without calibration on an integrated circuit whether or not its surface consists of metal, semiconductor or insulator or any combination of these. This independence of material properties is a rather unique property of thermal and mechanical interactions, and has very important practical implications. The lateral resolution of such a probe to first order is predicted to be close to the dimension of the tip. If a 100 Angstrom probe can be made, this should lead to lateral profiling resolution of the same dimension. It may be as interesting to do the profilometry at larger dimensions as well. Indeed, there are many applications for non-contacting profilometry at resolutions of 1000 Angstroms to 10 microns. Even with 1000 to 5000 Angstrom probe tips and resolution, the non-contacting feature makes this approach look very attractive when compared with the existing mechanical stylus approach which is generally destructive to the sample.

The use of a thermocouple is not the only way to sense the loaded temperature. A thermister can also be created at the junction by using a material at the tip which has electrical conductivity which depends strongly upon its temperature. The sensing would not be substantially different for either the thermocouple or thermister, and other approaches are possible, including optical.

The theory behind the approach of the present invention also predicts that if another coupling material is used, for example water, rather than air, the thermal impedance of the solid may begin to effect the temperature loading of the tip. Under this condition, the probe could be used to measure the thermal properties of the solids with high spacial resolution. High resolution images of the thermal properties of solids may be possible.

It is anticipated that the invention will find numerous important applications for viewing biological samples, viruses and small bacteria, and the like, where TEM (transmission electron microscope) contrast is very weak. For example, direct mapping of the topography of cell surfaces at the present time can only be done by freeze fracturing the cell, then viewing the crosssection of the cell in the electron microscope. The invention would enable non-destructive investigation of the cell surface. There are also many important physical characteristics of materials which manifest themselves on the surface as topographical information. The invention enables such manifested characteristics as strain and optical absorption to be measured. It leaves only to the imagination what new information may be extractible from the ability to profile with such high lateral and depth resolution.

Other and further features, objects advantages, and benefits of the invention will become apparent from the following description taken in conjunction with the following drawings. It is to be understood that both the foregoing general description and the following detailed description are exemplary and explanatory but not restrictive of the invention. The accompanying drawings which are incorporated in, and constitute a part of this invention illustrate one embodiment of the invention and, together with the description, serve to explain the principles of the invention in general terms. Throughout the drawings, like numerals refer to like parts.

DETAILED DESCRIPTION OF THE DRAWINGS

FIGS. 8 and 9 represent profiles of surface structures which have been achieved using the apparatus and techniques of the invention.

DESCRIPTION OF THE PREFERRED EMBODIMENTS

Figure 1:
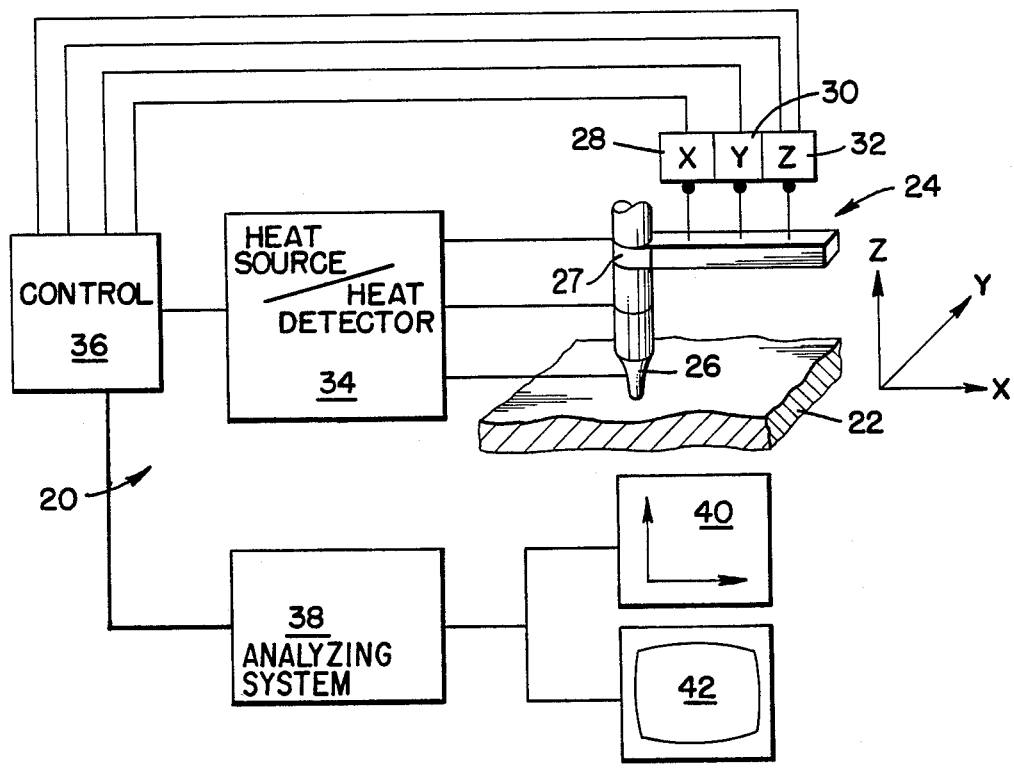
FIG. 1 shows schematically a block diagram of the essential parts of the apparatus for investigation of surface structures according to the invention.

Turn now to the drawings and initially to Figure 1 which generally depicts in block and diagrammatic form apparatus 20 which is appropriate to investigate surface structures 22 in accordance with the invention. Unlike the scanning tunneling microscope as disclosed in U.S. Pat. No. 4,343,993 mentioned above, the apparatus 20 does not require an isolated, ultra-high vacuum, ultra-low temperature environment for its operation. Indeed, the apparatus 20 is operable at normal room temperatures and pressures, although some degree of isolation may be desirable.

The sample surface structure 22 may be composed of any material, without restriction, whether the material is electrically conductive, insulative, or is semi- conductive. Even surfaces of liquids can be investigated so long as they are different from the environment of the probe. Furthermore, the roughness of the sample surface structure 22 can be extreme since the apparatus 20 is capable of investigating even the most irregular of surfaces.

As illustrated in FIG. 1, a probe 24 including a fine scanning tip 26 is poised only a short distance away from the sample surface structure 22. It will be appreciated that both the structure 22 and the scanning tip 26 are drawn schematically in exaggerated size. In any suitable manner, the structure 22 and the scanning tip 26 can be moved relative to each other in three dimensions. Symbolically, this is shown by three axes crossing rectangularly and designated by x, y, and z. For ease of illustration, the probe 24, in FIG. 1, is illustrated as being provided with a suitable drive mechanism 27, such as one having three piezo drives, 28, 30, and 32. Piezo drives 28 and 30 operate in the lateral dimensions x and y. For example, they may act on the probe 24 to move the tip 26 in those directions generally parallel to the surface structure 22. Alternatively, the probe 24 may be fixed and the surface structure 22 moved relative to the scanning tip 26. The vertical piezo drive 32 adjusts the relative positions of the surface structure 22 and scanning tip 26 in the z dimension.

Means for control of the probe 24 and for analyzing and indicating the investigation results are also represented schematically in FIG. 1. Specifically, measuring equipment 34 is part of the electronic control means and is connected to the probe 24 in an appropriate fashion as well as to the piezo drives 28, 30, and 32. A control system 36 is connected to the measuring equipment 34 and acts upon the vertical piezo drive 32. The measuring equipment 34 is connected to analyzing system 38 which, in turn, is connected to suitable display means, for example, to a plotter 40 and to a display screen 42.

Typically, the mechanical dimensions of the structure 22 and probe 24, as well as their possible ranges of adjustment are extraordinarily tiny. Also, the electronic control equipment must be able to operate in a precise manner and the measuring equipment must be extremely sensitive. The scanning tip 26 is typically moved above the sample surface structure 22 at a distance in the order of magnitude of about 10 Angstroms to 1000 Angstroms. A scanning tip 26 should not be permitted to strike against the surface structure 22 so as to avoid the possibility of damage to either element. At the same time the scanning tip 26 must not be so far removed from the surface structure 22 that the latter does not have any heat sinking capability with respect to the scanning tip 26.

Figure 2:
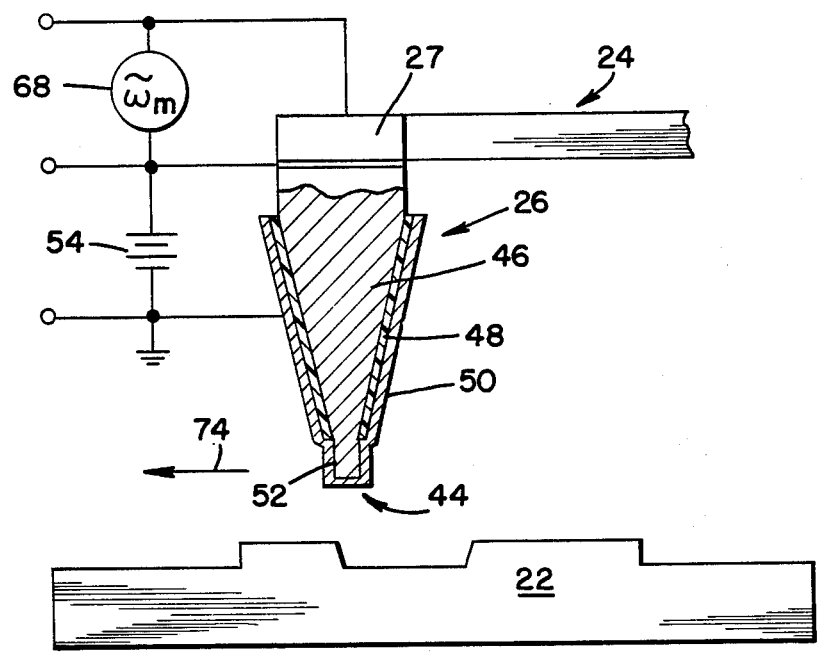
FIG. 2 is a diagrammatic representation of a probe including a fine scanning tip as it is moved across a surface structure to be investigated.

Turn now to FIG. 2 which diagrammatically illustrates the construction of the scanning tip 26. The scanning tip 26 is generally cylindrical in shape tapered down to an extreme end 44. A central structural element 46 may be of an electrically conductive material, such as tungsten, which can be controllably produced using electro-etching or electropolishing techniques, typically on the order of 100 Angstroms or less in diameter. The element 46 is electrically insulated with a thin layer of insulator or dielectric material 48 over all the regions of the structural element with the exception of a small region near the extreme end 44. One example of the dielectric material 48 may be material sold by Union Carbide Corporation, New York, New York under the trademark, "Parylene-C". Thereupon, the structural element 46 and dielectric layer 48 are coated with a thin electrically conducting layer 50, such as nickel which is ion beam sputtered onto the tip 26, and resulting in a thermocouple junction 52 adjacent the extreme end 44.

Figure 3:
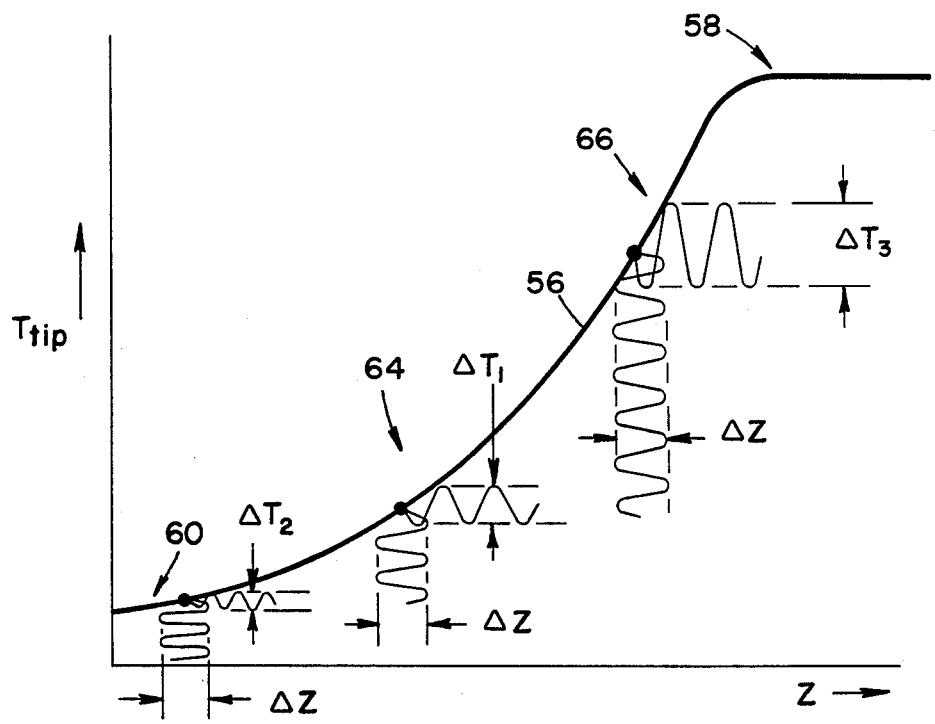
FIG. 3 is a graph which depicts a relationship between temperature of the fine scanning tip with distance from the surface structure to be investigated.

When an electrical current is driven through the thermocouple junction 52 as by an emf source 54, after a short initial period of time, the extreme end 44 of the scanning tip 26 arrives at a steady state temperature. The magnitude of the temperature depends upon the amount of thermal loading of the tip temperature caused by the surrounding environment. If the scanning tip 26 is then brought close to the surface structure 22, the temperature of the tip would also be loaded by the presence of the surface structure. Thus, as seen in FIG. 3, a curve 56 is a plot of tip temperature versus separation distance z from the sample surface structure 22, assuming a relatively hot tip and a relatively cold surface structure. Of course, the alternate situation can be envisioned in which the tip is relatively cold and the surface structure relatively hot. The curve 56 extends from a region 58 at which a steady state temperature is achieved when the tip is remote from the surface structure 22 down to a region 60 of minimum temperature when the tip is proximate to the surface structure.

It will be recognized that the conductivity of the surface structure 22 is much greater than that of the air or surrounding medium in which probe 24 is located. Thus, as the scanning tip 26 is brought into closer proximity with the surface structure, more heating flux leaves the tip because it is much more conductive that is, is a much more effective heat sink, than the surrounding air. The preceding discussion assumes that the steady state temperature is greater than that of the surface structure, but in fact the steady state temperature may just as likely be less than that of the surface structure. Thus, the term "heat source" is also broadly intended to include a "heat sink" should such an arrangement be desired.

It will be understood that the operation of the invention is not to be limited only to the customary situation in which the surrounding environment is gaseous, whether air or otherwise, and the surface structure is solid. Indeed, the invention is applicable to other situations such as where the surrounding environment and the surface structure are dissimilar liquids, or where the surrounding environment is gaseous and the surface structure is liquid.

However, it will be recognized that the scanning tip 26 is not only subject to the heat sinking ability of the surface structure 22, but is also subject to environmental temperature changes. For example, steady state temperatures which FIG. 3 indicates as occurring in the region 58 can increase if the environmental temperature increases, or conversely, decrease if the environmental temperature decreases. However, the apparatus 20 is so designed as to be unaffected by such environmental changes.

Specifically, the analyzing means 38 includes suitable electronic circuitry having the ability to differentiate finite values of the curve 56 to thereby generate a curve 62 (FIG. 4) representing the rate of change of the temperature at any given distance z from the surface structure 22. In order to obtain an output having the characteristics of the curve 62, the scanning tip 26 is vibrated or oscillated by a small amplitude in the order of hundreds of Angstroms. To this end, the scanning tip 26 is energized by a cyclic emf source 68 which causes oscillations in the piezo drive 32. This cyclic emf source is operated at a frequency $\omega_m$.

Thus, as seen in FIG. 3, if the scanning tip 26 is oscillated over a range $\Delta z$ in an intermediate region 64 of the curve 56, it results in a modulation of the temperature $\Delta T_1$. By same token, for the same amplitude of vibration, $\Delta z$ in the region 60, temperature modulation $\Delta T_2$ is achieved, and in a region 66 intermediate the regions 58 and 64, for the same range of vibration, a temperature modulation $\Delta T_3$ is achieved.

Thus, it will be seen from FIG. 3, that $\Delta T_2$ is much smaller than $\Delta T_1$, while $\Delta T_3$ is much larger than $\Delta T_1$. Thus, the rate of temperature variation increases with increasing distance of the scanning tip 26 from the surface structure 22. Furthermore, this gradient of temperature variation does not change appreciably with temperature changes in a surrounding environment.

Figure 5:
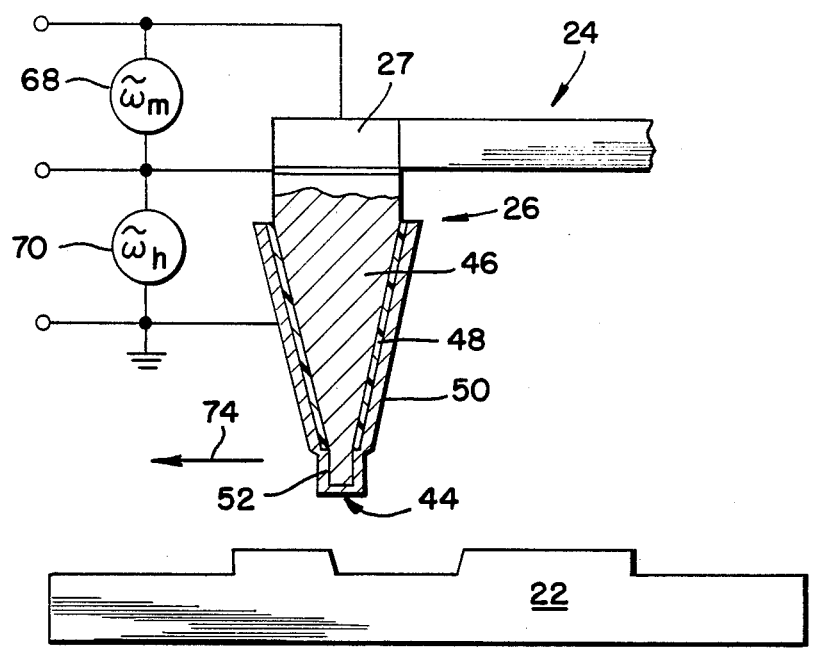
FIG. 5 is a diagrammatic representation, similar to FIG. 2, illustrating another embodiment of the invention.

Turn now to FIG. 5 which depicts a slightly modified construction for the probe 24.

Because of the miniature size of all of the components comprising the invention, substantial efforts must be made to eliminate potential sources of noise. A superior method of achieving this end result is to modulate the heating of the tip as well as the movement imparted to the tip and to assure that the frequencies employed in these instances are different. By varying the heat at the scanning tip 26 at the frequency $\omega_h$ as can be achieved with a cyclic emf source 70, and by varying the spacing between the tip and the surface structure 22 at the frequency $\omega_m$, components of the temperature fluctuation of the tip will exist either at the frequency $\omega_m - \omega_h$ or at the frequency $\omega_m + \omega_h$ and can be detected by a temperature sensor which may be of the form of the thermocouple junction 52 located at the extreme end 44 of the scanning tip 26.

As seen in FIGS. 2 and 5, the scanning tip 26 is moved laterally above the surface structure 22 in the direction of an arrow 74 at a distance in the order of magnitude of about 10 Angstroms to 1000 Angstroms. While the scanning tip 26 should not strike against the surface structure 22 to thereby prevent damage either to itself or to the scanning structure, it also should not be removed to such a remote position away from the surface of the surface structure that temperature variations no longer exist. The diameter or width of the extreme end 44 of the scanning tip 26 may be generally in the range of 100 Angstroms to 5000 Angstroms. Applying known fabrication techniques, it is anticipated that the diameter or width of the extreme end 44 might eventually be less than 100 Angstroms. It is noteworthy that the scanning tip 26 does not have the drawback of the scanning tunneling microscope which has only a narrow focus and does not readily accommodate rapid, severe changes in topography. That is, the scanning tip 26 can readily detect rapid and severe changes in topography by reason of its ability to sense around an arc of approximately 270°.

Figure 4:
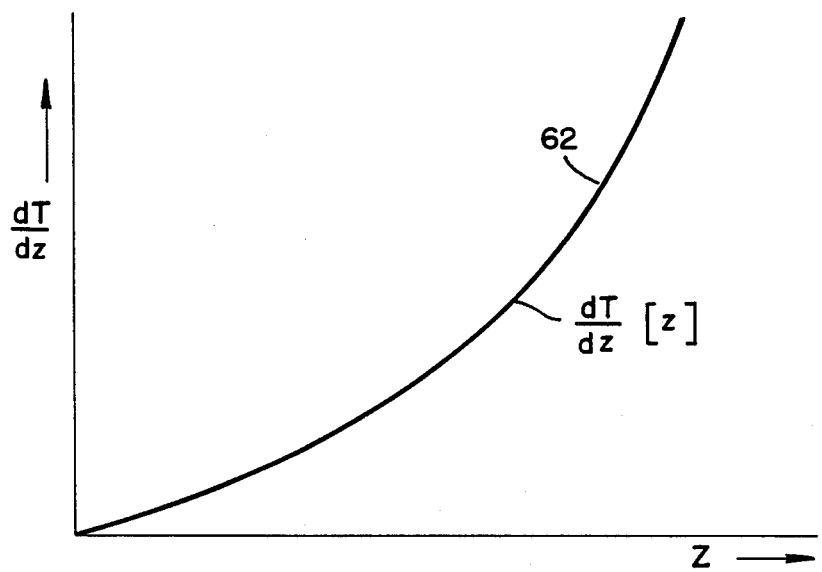
FIG. 4 is a graph depicting a curve which is the derivative of the curve presented in FIG. 3.

It will be appreciated that the vertical piezo drive 32 must be particularly accurate because, as seen in FIG. 4, temperature variation depends heavily upon the separation distance z from the surface structure 22. The drive mechanism 27 should not only be adjustable over small distances in all dimensions, but set positions should also be definite and reproducible. The piezo drives 28, 30, and 32 are capable of such operation, although other suitable drive means can be employed. The exact position of the scanning tip 26 can be determined from the values set, that is, from the voltages applied to the piezo drives.

The new apparatus 20 for the investigation of surface structures not only delivers data about individual measuring points but also gives information about a whole area of a sample surface within a short time period. It operates much like a scanning microscope. The sample surface is investigated in raster lines one after the other, and the whole image is composed of the scanning lines of the scanning pattern. During the scan, the drive means of a first lateral dimension is operating for a raster line, while the drive means of the transverse other lateral dimension is kept fixed. After a lateral shift of about a line width, the next line is scanned by the first drive means and so forth.

While scanning with a tip 22 poised above a sample surface structure 22, a certain danger exists of making inadvertent contact between the tip and sample because roughness of the surface may be on the order ot magnitude of the vertical distance of the tip above the sample. Such involuntary contact should be avoided. The apparatus of the invention avoids such danger automatically. The scan operation is defined in the lateral dimensions. However, the tip's vertical distance is variable. The measuring method itself, or the control method, automatically keeps a correct distance between the tip and the sample surface. By continuously measuring temperature variation at the thermocouple junction 52, the separation distance z of the tip 26 can be determined at all times from the graph in FIG. 4. The operation can be conducted such that the temperature variation in the tip is kept constant by fine adjustment of the tip's vertical distance above the sample to follow the surface contours as the lateral scan is made. The sensed temperature signal may be used to control the vertical distance of the apparatus if temperature variation is kept constant. The apparatus is controlled during scan in a lateral dimension according to an electrical variable which is proportional to the temperature variation. A temperature variation is measured and kept constant by fine adjustment of the vertical drive in the z dimension by means of a closed loop control system.

The scanning pattern is preferably a line raster whereby the area is scanned in a first lateral dimension (x) in straight parallel lines, one after the other. The second lateral dimension (y) is the other scanning parameter. The vertical distance (dimension z) is controlled with a feedback system in accordance with the measured variable which is proportional to the temperature variation. Since the position of a piezo drive is proportional to the piezo voltage, or to the respective drive current, the drive currents of the three piezo electrical drive means represent values equivalent to the position of the tip in each dimension. Generally, the coordinates are cartesian coordinates with three orthogonal axes. However, curved scanning measured and kept constant by fine adjustment of lines is also permitted, if the lines are reproducible.

Data analysis is made as a three dimensional representation. Both lateral dimensions can easily be shown in the plotter 40 or on the display screen 42. A suitable representation must be chosen, however, for the third dimension. One possibility is to represent the measuring values as a set or family of curves z(x) as a function of parameter y. Another possibility is to show the z values as brightness steps at point x, y. A corresponding graphical representation may comprise points with different areas of other symbols. When the representation occurs on a screen, the brightness of the cathode ray tube may be controlled according to the values of the third dimension.

The tip passes across the surface of the sample at a vertical distance such that during scan the temperature variation at the thermoelectric junction 52 is controlled to a constant value. This means that during the scanning movement, the tip is following all unevenness and roughness of the sample surface at a constant distance therefrom. The drive current of the vertical piezo drive 32 thus is a true image, or replication, of the surface structure. The image, or replication, produced by the apparatus 20 is an extremely enlarged image of the sample surface.

Figure 6:
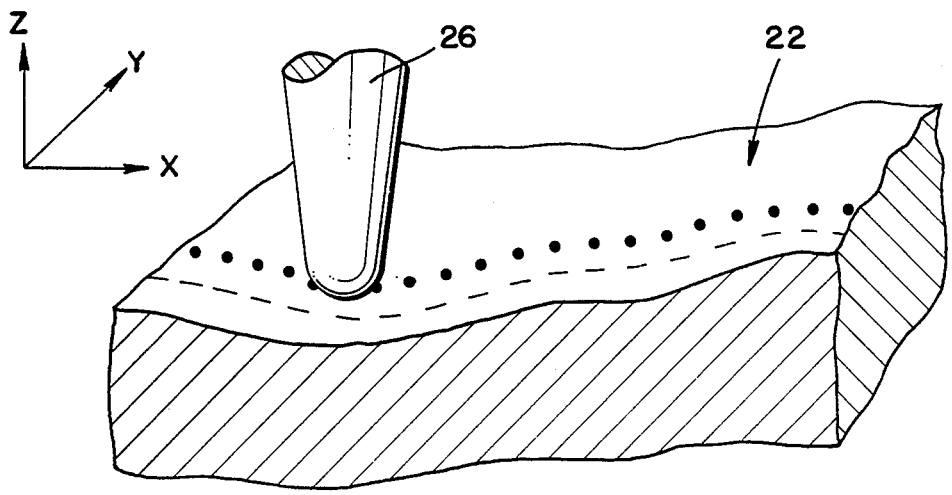
FIG. 6 is a detailed perspective view, partly in section, illustrating repeated lateral scanning of the surface to be investigated with parallel raster scan lines.

After completing the scanning of a raster line in a first lateral dimension (x), the tip 26 is shifted in the transverse second lateral dimension (y) by about the thickness of a raster line. Subsequently, another raster line is scanned parallel to that first line. By repeated lateral scanning of parallel raster lines, the whole sample surface will be scanned, line by line. In FIG. 6 both elements 22 and 26 are diagrammatically shown much enlarged. At the sample surface, the dashed line indicates the path of the shadow of tip 26 over the surface of the sample surface structure 22. The dotted line indicates the path of the tip itself at a distance over the surface determined by the constant temperature variation. The axis system x, y, z indicates the coordinates of the dimensions. For example, scanning may occur in the x dimension.

Figure 7:
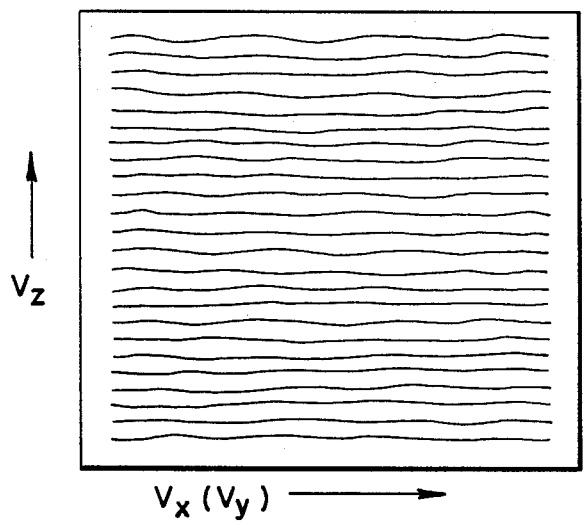
FIG. 7 illustrates schematically a practical three-dimensional plot of the investigation results either as values of the tip position or as the proportional piezo voltages of the piezo drives.

Between repeated scans, the tip is shifted in the y dimension about the thickness of a raster line in each case. Fine adjustment by the vertical drive means automatically controls the z dimension position of the tip so as to maintain a constant temperature variation. The results of the scan performed by the scanning tip 26 are displayed by plotting the drive current or piezo voltages as a set of curves representing three dimensions. These measured currents or voltages correspond to the position dimensions of the fine tip 26 in three coordinate directions. For example, FIG. 7 shows the z direction piezo voltage Vz as a function of the x direction piezo voltage Vx for each of a family of different y direction piezo voltages Vy. The family of curves of FIG. 7 is then a true enlarged image, or replication, of the sample surface structure.

The invention is operable in a wide range of surrounding atmospheres or media, although air or the inert gases are preferred. Even using such preferred atmospheres, however, it will be appreciated that at high resolution (that is, as the scanning tip 26 is moved closer and closer to the surface structure 22 being investigated), the distance between the tip and the surface structure actually becomes less than the mean free path of atoms or molecules of the surrounding atmosphere. As a result, the thermal conductivity of the surrounding atmosphere becomes reduced. In order to prevent this occurrence, the pressure of the surrounding atmosphere is preferably increased. This serves to reduce the mean free path of the atoms or molecules of the media and thereby maintain the previous level of thermal conductivity.

Figure 10:
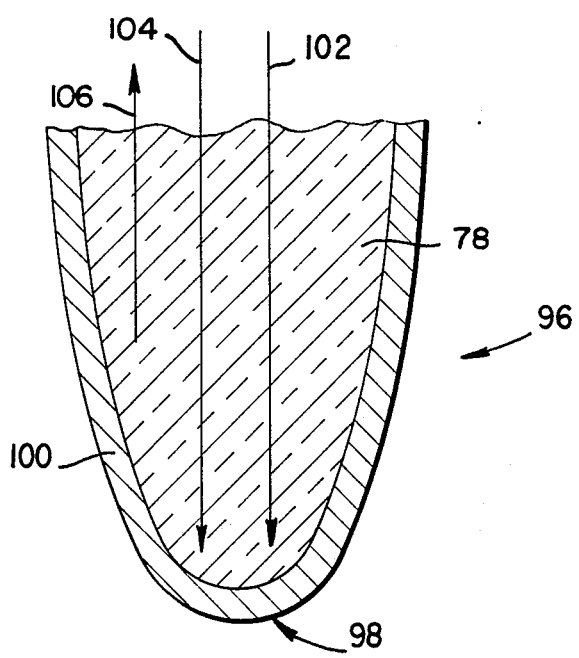
FIG. 10 is a detail vertical cross-section view of a modified fine scanning tip for use with the invention.
Figure 9:
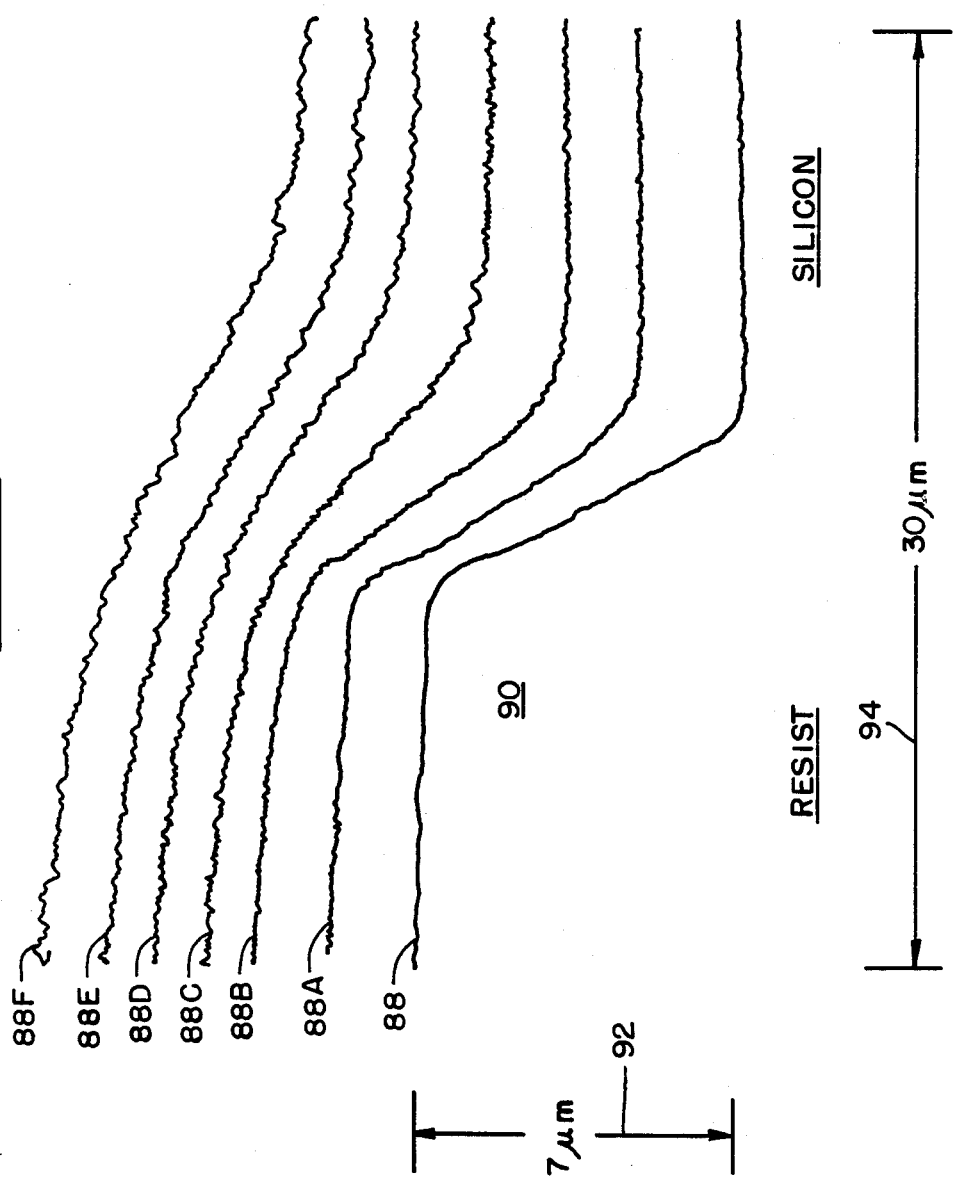

The illustrations presented in FIGS. 9 and 10 are representative of the results which can be achieved when the apparatus and techniques of the invention are employed to investigate a surface structure.

FIG. 8, by way of example, depicts a profile 76 which has been obtained when the scanning tip 26 has performed an investigation of a surface structure 78 along a single line scan. A scale 80 represents a measure of 1000 Angstroms in the vertical dimension and a scale 82 represents a measure of one micron in the lateral dimension. In this instance, the scanning tip has a tip diameter of approximately 1000 Angstroms and the surface structure is a silicon wafer on which a 1000 Angstrom thick aluminum film has been deposited. The noise level indicated by the heaviness of the line depicting the profile 76 demonstrates vertical resolution achieved by the probe 24. Furthermore, spikes 84 and 86 occurring in the profile 76 portray actual topography such as burrs which may have occurred during the deposition process. These spikes illustrate the capability of the probe 24 to resolve very small structures. For example, the half width of left hand spike 84 (the smaller of the two spikes) represents the lateral resolution achieved, or approximately 1000 Angstroms.

FIG. 9, by way of example, depicts a profile 88 which has been obtained when the scanning tip 26 has performed an investigation of a surface structure 90, again along a single line scan, but at different heights above the surface structure. A scale 92 represents a measure of microns in the vertical dimension and a scale 94 represents a measure of 30 microns in the lateral dimension. Again, the scanning tip 26 has a tip diameter of approximately 1000 Angstroms. The surface structure 90 is a 7 micron photoresist insulating layer deposited on a silicon wafer. The profiles 88A–88F represent successive scans at ever increasing heights above the surface structure 90.

It is apparent from a study of FIG. 9 that the resolution in the lateral dimension is a function of the closeness of the tip 26 to the surface structure. Resolution becomes increasingly good as the distance between the tip and the surface structure decreases and simultaneously the signal to noise ratio which represents vertical resolution increases dramatically.

Another embodiment of the invention is illustrated in FIG. 10 which illustrates a modified scanning tip 96. In this instance the scanning tip 96, which is dimensionally similar to the scanning tip 26, has a central structural element 98 which is of optical quality glass or plastic material with an outer layer 100 of metallic coating, for example, chromium. In a known fashion, a laser beam 102 is directed onto an extreme end of the scanning tip 96. The laser beam impinges on the coating which serves to absorb power from the beam and supply heat into the central structural element 98. As with the constructions illustrated in FIGS. 2 and 5, the scanning tip 96 is also provided with a temperature sensor effective to measure the temperature of the scanning tip 96 and to communicate that temperature to the control system 36. To this end, a second beam 104 is directed at the metallized surface at the extremity of the tip 98. The beam 104 is then reflected off the metallized surface, as represented by an arrow 106, and is phase modulated by the temperature variation in the tip. This phase modulation can be detected by standard interferometric techniques, preferably in a fiber optic interferometer. In all other respects, apparatus utilizing the modified scanning tip 96 for purposes of the invention would be as previously described.

While the preferred embodiments of the invention have been disclosed in detail, it should be understood by those skilled in the art that various modifications may be made to the illustrated embodiments without departing from the scope as described in the specification and defined in the appended claims.

Having thus described our invention, what we claim as new, and desire to secure by Letters Patent is:

1. Apparatus for investigating surface structures present on the surface of a sample to be investigated irrespective of the materials involved comprising:
   probe means including a fine scanning tip;
   means for relatively positioning said scanning tip and the surface to be investigated;
   a heat source for heating said scanning tip to a controlled temperature when said scanning tip is remote from the sample surface; temperature sensing means at said scanning tip for detecting variations in the tip temperature when said scanning tip is moved to a separation distance in close proximity with the sample surface;
   means for scanning said scanning tip across the sample surface in close proximity therewith;
   means for automatically controlling the separation distance between said scanning tip and the sample surface in response to the temperature variations such that the temperature variations remain substantially constant during scanning; and
   means for graphically displaying the spatial coordinates of said scanning tip to produce a topographical map of the surface.

2. Apparatus as set forth in claim 1 wherein said means for positioning comprises:
   a piezo electric drive means acting in the direction along which the separation distance between said scanning tip and the sample surface is controlled, said direction being the z direction.

3. Apparatus as set forth in claim 1 wherein said means for scanning comprises:

piezo electric drive means acting in directions x and y, both being perpendicular to the z direction.

4. Apparatus as set forth in claim 3 wherein said means for graphically displaying the spatial coordinates comprises: means for graphically displaying the drive current or voltage of the z direction piezo electric drive means as a function of the drive currents or voltages of the x and y direction piezo electric drive means.

5. Apparatus as set forth in claim 2 wherein said means for automatically controlling the separation distance between said scanning tip and the sample surface comprises:
a feedback system controlling said z direction piezo electric drive means in response to the measured temperature variation.

6. Apparatus as set forth in claim 2 wherein said piezo electric drive means acting in the z direction includes:
means for vibrating said scanning tip transversely of the sample surface at a first frequency,
whereby said scanning tip is unaffected by environmental temperature changes.

7. Apparatus as set forth in claim 6 wherein said heat source includes:
a thermocouple provided at an extremity of said scanning tip; and
oscillating means for directing an electrical current through said thermocouple at a second frequency which is different from said first frequency.

8. Apparatus as set forth in claim 1 wherein said scanning tip includes:
a central structural element composed of conductive material and having an extreme end;
a layer of dielectric material coated on said central structural element except on said extreme end; and
a layer of electrically conducting material coated over said layer of dielectric material and on said extreme end of said central structural element.

9. Apparatus as set forth in claim 8 wherein:
said temperature sensing means includes a thermocouple junction formed at the location at which said central structural element and said layer of electrically conducting material interface.

10. A method of investigating surface structures irrespective of the materials involved comprising the steps of:
applying heat to a scanning tip so that it achieves a steady state temperature when it is remote from the surface of a sample to be investigated;
moving the scanning tip transversely of the sample surface to a separation distance in close proximity therewith;
scanning the scanning tip across the sample surface;
sensing variations in temperature of the scanning tip from the steady state temperature as the scanning step proceeds;
automatically controlling the separation distance between the scanning tip and the sample surface in response to the temperature variations such that the temperature variations remain constant during the scanning step; and
graphically displaying the spatial coordinates of the scanning tip to produce a topographical map of the sample surface.

11. A method as set forth in claim 10 wherein the automatically controlling step includes the steps of:
generating a first electrical signal proportional to an initial temperature variation between the steady state temperature of the scanning tip and the temperature of the scanning tip as it is initially moved to a separation distance in close proximity to the sample surface; and
generating a continuing series of second electrical signals proportional to subsequent temperature variations as the scanning step proceeds;
comparing each of the continuing series of second electrical signals with the first electrical signal; and
continually adjusting the separation distance between the scanning tip and the sample surface such that said continuing series of second electrical signals are equal to the first electrical signal.

12. A method as set forth in claim 11 wherein the step of moving the scanning tip transversely of the sample surface is performed by a first drive means; and wherein the step of scanning the scanning tip is performed by a second drive means.

13. A method as set forth in claim 12 wherein the first and second drive means are each piezo-electric drivers.

14. A method as set forth in claim 10 wherein:
the temperature of the scanning tip at the separation distance remote from the sample surface is different than the temperature of the scanning tip at the separation distance in close proximity thereto when the amount of heat applied to the scanning tip is substantially constant.

15. A method as set forth in claim 10 including the step of:
oscillating the scanning tip transversely of the sample surface when the scanning tip is at a separation distance in close proximity to the sample surface, whereby the scanning tip is unaffected by environmental temperature changes.

16. A method as set forth in claim 15 wherein:
the step of oscillating the scanning tip is performed at a frequency in the range of one to $10^5$ hertz and at an amplitude in the range of $10^2$ to $10^6$ Angstroms.

17. A method as set forth in claim 10 wherein the step of applying heat to the scanning tip includes the steps of:
providing a thermocouple at an extremity of the scanning tip; and
directing an electrical current through the thermocouple at a frequency in the range of zero to $10^6$ hertz; and
wherein the step of sensing variations in temperature includes the step of: sensing variations in average temperature of the scanning tip as the scanning step proceeds.

18. A method as set forth in claim 10 including the step of:
oscillating the tip transversely of the sample surface at a first frequency when the scanning tip is at a separation distance in close proximity to the sample surface; and
wherein the step of applying heat to the scanning tip includes the steps of:
providing a thermocouple at an extremity of the scanning tip; and
directing an electrical current through the thermocouple at a second frequency different from the first frequency.

19. A method as set forth in claim 18:
wherein the step of oscillating the scanning tip is performed at a first frequency in the range of one to $10^5$ hertz and at an amplitude in the range of one to $10^6$ Angstroms; and wherein the step of directing an electrical current through the thermocouple is performed at a second frequency in the range of zero to $10^6$ hertz.

20. A method as set forth in claim 10 wherein the step of applying heat to the scanning tip includes the step of: directing a laser beam at the scanning tip.

21. A method as set forth in claim 20:
wherein the step of directing a laser beam at the sensing tip is performed at a frequency in the range of zero to $10^6$ hertz; and
wherein the step of sensing variations in temperature includes the step of sensing variations in average temperature of the scanning tip as the scanning step proceeds.

* * * * *